(12) United States Patent
Hahn

(10) Patent No.: US 8,896,309 B2
(45) Date of Patent: Nov. 25, 2014

(54) SPINE COIL UNIT

(75) Inventor: Heinz Hahn, Möhrendorf (DE)

(73) Assignee: Siemens Aktiengesellschaft, München (DE)

( * ) Notice: Subject to any disclaimer, the term of this patent is extended or adjusted under 35 U.S.C. 154(b) by 819 days.

(21) Appl. No.: 12/954,267

(22) Filed: Nov. 24, 2010

(65) Prior Publication Data

US 2012/0126815 A1   May 24, 2012

(51) Int. Cl.
G01V 3/00        (2006.01)
G01R 33/34       (2006.01)
G01R 33/36       (2006.01)
G01R 33/48       (2006.01)
G01R 33/3415     (2006.01)

(52) U.S. Cl.
CPC ...... *G01R 33/34007* (2013.01); *G01R 33/3415* (2013.01); *G01R 33/36* (2013.01); *G01R 33/3692* (2013.01)
USPC ............ 324/318; 324/309; 324/321; 600/410

(58) Field of Classification Search
CPC . G01R 33/0052; G01R 33/285; G01R 33/287
USPC ............................ 324/300–322; 600/407–464
See application file for complete search history.

(56) References Cited

U.S. PATENT DOCUMENTS

| 5,059,906 | A  | * | 10/1991 | Yamanaka ............... | 324/318 |
| 6,317,619 | B1 | * | 11/2001 | Boernert et al. ........ | 600/410 |
| 6,498,489 | B1 | * | 12/2002 | Vij ......................... | 324/322 |
| 7,009,398 | B2 | * | 3/2006  | Hahn et al. ............ | 324/318 |
| 8,290,569 | B2 | * | 10/2012 | Piron et al. ............ | 600/415 |
| 8,294,460 | B2 | * | 10/2012 | Driemel .................. | 324/307 |
| 8,324,899 | B2 | * | 12/2012 | Hoogeveen ............. | 324/318 |

* cited by examiner

*Primary Examiner* — Melissa Koval
*Assistant Examiner* — Emily Chan
(74) *Attorney, Agent, or Firm* — Lempia Summerfield Katz LLC

(57) ABSTRACT

In order to increase the speed at which a user of a magnetic resonance imaging (MRI) system may electrically or optically connect and physically attach a spine coil unit to the MRI system, the spine coil unit includes a connector extending away from a side of a spine coil housing. The spine coil unit is positioned on a patient table of the MRI system and moved along the patient table of the MRI system adjacent to or in physical contact with a corresponding MRI system-side connector. A lever rotatably attached to the spine coil housing may be rotated into a corresponding recess in the MRI system to physically attach and electrically or optically connect the connector of the spine coil housing and/or to positionally fix the spine coil housing relative to the MRI system-side connector.

18 Claims, 4 Drawing Sheets

SPINE COIL UNIT

FIELD

The present embodiments relate to a spine coil unit for a magnetic resonance imaging system.

BACKGROUND

Magnetic resonance imaging (MRI) is a non-invasive imaging technique that may be used to display detailed tissue structures in the body of a patient. The displayed tissue structure may provide valuable information assisting in the diagnosis and treatment of various medical conditions.

An MRI system may include three components or subsystems: a magnet with a main magnetic field, a gradient system, and a radiofrequency (RF) system. The main magnetic field produced by the magnet aligns the nuclear magnetization of atoms in the body of the patient. The gradient system spatially varies the main magnetic field with corresponding pairs of gradient coils, such that the position of a slice to be imaged may be precisely located. The RF system includes antennas (e.g., coils) that are used to send RF pulses (e.g., transmitter coils) and/or receive magnetic resonance (MR) signals (e.g., receiver coils). The RF pulses produce an electromagnetic field that flips or changes the alignment of the nuclear magnetization of the atoms. When the electromagnetic field is turned off, the nuclear magnetization of the atoms decays to the natural alignment of the atoms within the main magnetic field, and the atoms release excess stored energy. When the atoms release the excess stored energy, the atoms give off MR signals that are received by the receiver coils of the RF system and are used to construct image slices. The signal strength in a receiver coil depends on the volume of excitation in the coil and the distance to the object to be measured.

The MRI system may include RF coil units optimized (e.g., sized, shaped and positioned) for imaging different body parts of a patient. A spine coil unit including at least one RF coil may be positioned on a patient table of the MRI system to image the spine of the patient. MR signals received by the RF coil of the spine coil unit may be transmitted using one or more electrical or optical cables in communication with the RF coil. A user of the MRI system (e.g., a doctor or nurse) physically attaches (e.g., plugs) connectors of the one or more electrical or optical cables to corresponding MRI system-side connectors, such that the MR signals received by the RF coil of the spine coil unit are transmitted to the MRI system for further processing. If body parts other than the spine are to be imaged, the user may unplug the spine coil unit, transfer the spine coil unit to a storage location and electrically connect another RF coil unit (e.g., a breast coil unit) to the MRI system.

SUMMARY

In order to increase the speed at which a user of a magnetic resonance imaging (MRI) system may electrically or optically connect and physically attach a spine coil unit to the MRI system, the spine coil unit includes a connector extending away from a side of a spine coil housing. The spine coil unit is positioned on a patient table of the MRI system and moved along the patient table of the MRI system adjacent to or in physical contact with a corresponding MRI system-side connector. A lever rotatably attached to the spine coil housing may be rotated into a corresponding recess in the MRI system to physically attach and electrically or optically connect the connector of the spine coil housing and/or to positionally fix the spine coil housing relative to the MRI system-side connector.

In one embodiment, an RF coil unit includes a coil housing including a first side, an RF coil disposed in the coil housing, a lever movably attached to the coil housing, and a rigid coil connector extending away from the first side of the coil housing. The rigid coil connector is in communication with the RF coil of the coil housing.

In another embodiment, a spine coil unit includes a spine coil housing and an RF coil disposed in the spine coil housing. The RF coil is configured to receive magnetic resonance signals emitted by a patient supported by the spine coil housing. The spine coil unit also includes a lever rotatably attached to the spine coil housing, and a coil connector physically connected to the spine coil housing and in communication with the RF coil of the spine coil housing. The lever is operable to be rotated into a corresponding recess in a support of an MRI system, such that the position of the spine coil housing is fixed relative to the position of a connector of the MRI system.

In yet another embodiment, a method of using a coil unit includes positioning the coil unit on a patient table of an MRI system, the coil unit including an RF coil. The method also includes electrically or optically connecting the coil unit to the MRI system and positioning a lever rotatably attached to the coil unit into a corresponding recess in a support of the MRI system, such that the electrically or optically connecting is maintained in place by the lever.

DETAILED DESCRIPTION OF THE DRAWINGS

In order to conduct signals out of local coils into a magnetic resonance imaging (MRI) system, plugs of the local coils are integrated directly with a housing of the coils. A counterpart plug panel is mounted fixedly on a patient table of the MRI system. The contour of the patient table centers the local coil with the plug panel. The coil is thrust horizontally on the table into the plug panel and locked solidly to the plug panel with the aid of a toggle lever (e.g., direct connect).

Figure 1:
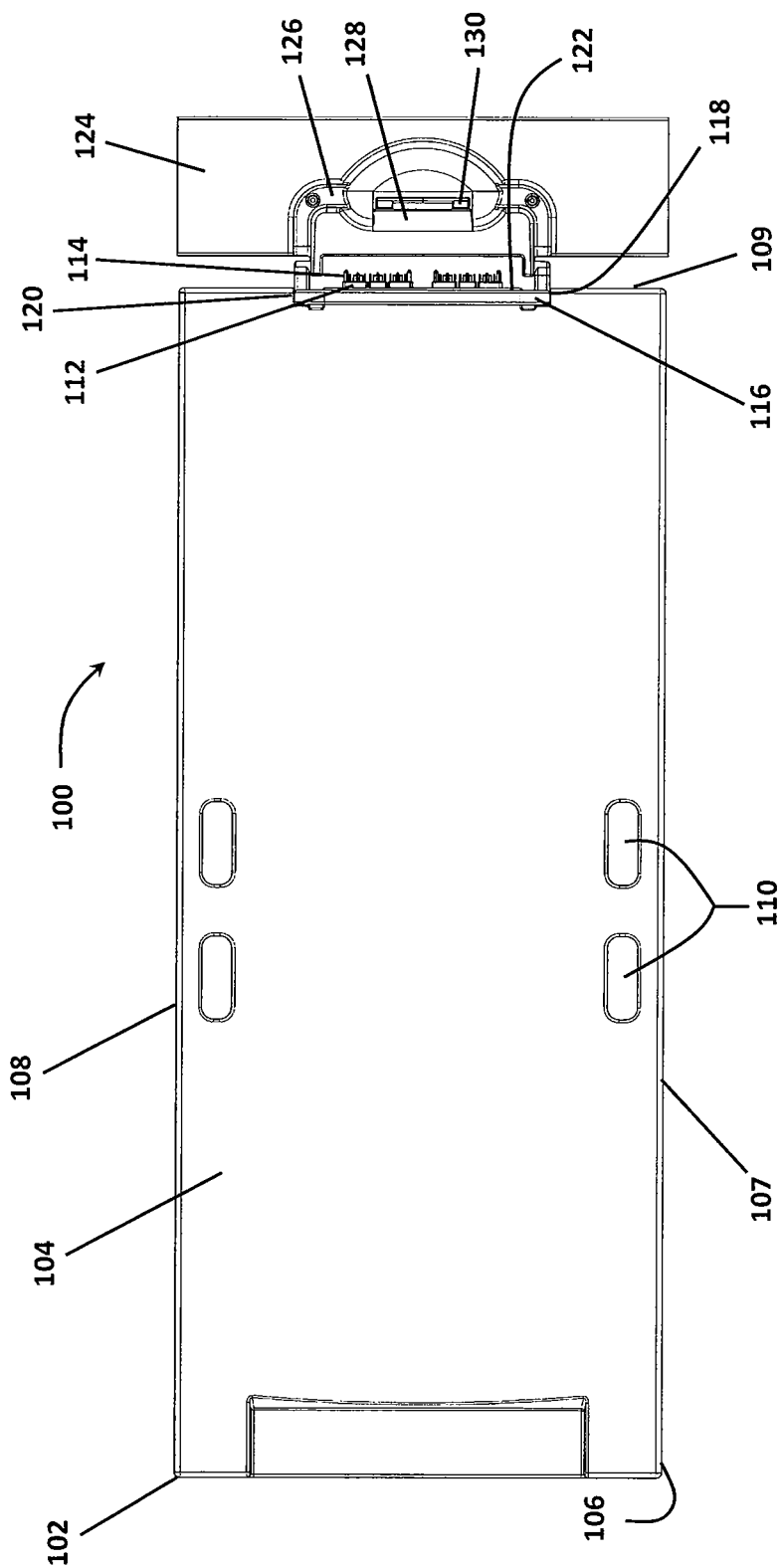
FIG. 1 illustrates a top view of one embodiment of a spine coil unit in an unlocked position.

FIG. 1 illustrates a top view of one embodiment of a spine coil unit 100 for a magnetic resonance imaging (MRI) system. The spine coil unit 100 includes a spine coil housing 102. The spine coil housing 102 includes a top surface 104, a bottom surface 106, a first side 107, a second side 108 and a third side 109. The top surface 104 of the spine coil housing 102 may be concave, while the bottom surface 106 of the spine coil housing 102 may be convex. In one embodiment, the bottom surface 106 of the spine coil housing 102 is shaped to match the shape of a top surface of a patient table of the MRI system. In another embodiment, the top surface 104 of the spine coil housing 102 and/or the bottom surface 106 of the spine coil housing 102 are flat. A cross-section along the length of the spine coil housing 102 may be generally rectangular, for example. "Generally" allows for rounded corners and other shapes. In one embodiment, the length of the spine coil housing 102 is approximately 120 cm, the width of the spine coil housing 102 is approximately 49 cm, and the height of the spine coil housing 102 is approximately 6.3 cm, but other distances and shapes may be used.

The spine coil housing 102 may be made of any number of MRI safe materials (i.e., materials that do not produce proton or magnetic signals) including, for example, polycarbonate. The spine coil housing 102 may be hollow with structural supports extending from the top surface 104 of the spine coil housing 102 to the bottom surface 106 of the spine coil housing 102, spaced along the length and/or the width of the spine coil housing 102. In another embodiment, at least part of the length of the spine coil housing 102 is solid polycarbonate.

One or more radiofrequency (RF) coils (not shown) are located within the spine coil housing 102. The spine coil housing 102 may include RF transmit coils and/or RF receive coils (e.g., 32 RF receive coils). The RF receive coils of the spine coil housing 102 may be surface coils and/or volume coils, for example. In one embodiment, the RF receive coils may be arranged in RF receive coil arrays (e.g., four RF receive coils per array). The RF receive coils of the spine coil housing 102 may be made of any number of electrically conducting materials including, for example, copper. The RF receive coils may be spaced along the length and the width of the spine coil housing 102, such that magnetic resonance (MR) signals may be received from the back side of the body (e.g., the spine) of a patient during MRI examination. In one embodiment, the RF receive coils may be positionally fixed within the spine coil housing 102. For example, the RF receive coils may be embedded within a solid part of the spine coil housing 102 or may be physically attached to an internal surface of the spine coil housing 102. In another embodiment, the RF receive coils may be movable relative to the spine coil housing 102.

The spine coil housing 102 may include a plurality of openings 110 (e.g., four openings) that extend from the top surface 104 of the spine coil housing 102, at least partly into the spine coil housing 102. The plurality of openings 110 are shaped and sized as hand holds. The plurality of openings 110 may also be used to transfer the spine coil unit 100 to and from the patient table of the MRI system, and to position the spine coil unit 100 along the patient table of the MRI system.

The spine coil housing 102 may include a printed circuit board (PCB; not shown) supported by or physically attached to an internal surface of the spine coil housing 102. The PCB may be a multilayered PCB, for example. One or more low-noise amplifiers (e.g., 32 low-noise amplifiers) are electrically connected to the PCB of the spine coil housing 102. The MR signals received by the RF receive coils of the spine coil housing 102 may be weak; the one or more low-noise amplifiers may reduce noise and interference signals (e.g., filter), while also amplifying the voltage (e.g., amplify) of the MR signals. In one embodiment, the PCB of the spine coil housing 102 includes the same number of low-noise amplifiers as the number of RF receive coils. Alternatively, the PCB of the spine coil housing 102 may include more or fewer low-noise amplifiers than the number of RF receive coils of the spine coil housing 102. The PCB of the spine coil housing 102 may include any number of different, additional, fewer, or other electrical hardware components such as, for example, doubly balanced mixers, analog to digital converters, specialized processors (e.g., application specific integrated circuits (ASICs)), generalized processors, flash memory, resistors and capacitors electrically connected to the PCB of the spine coil housing 102. The RF receive coils of the spine coil housing 102 may be fabricated on the PCB of the spine coil housing 102 and are electrically connected to at least some of the electrical hardware components via traces on the PCB (e.g., each RF receive coil of the spine coil housing 102 may be electrically connected to one low-noise amplifier electrically connected to the PCB of the spine coil housing 102). The RF receive coils of the spine coil housing 102 may be fabricated on the PCB of the spine coil housing 102 using lithography or another mask-driven process, for example. In one embodiment, the spine coil housing 102 includes a plurality of PCBs.

In another embodiment, the plurality of RF receive coils of the spine coil housing 102 are electrically connected to inputs of the PCB of the spine coil housing 102 via a plurality of corresponding electrical cables (e.g., input electrical cables). An electrical cable may be electrically connected to (e.g., soldered to) one or more corresponding RF receive coils of the spine coil housing 102 and an input of the PCB of the spine coil housing 102. The input electrical cables may be coaxial cables and/or wires, for example. The input electrical cables of the spine coil housing 102 may be electrically connected to and physically attached to one or more electrical cable input connectors (e.g., coaxial cable input connectors) electrically connected (e.g., soldered) to the PCB of the spine coil housing 102.

One or more output connectors (e.g., electrical cable output connectors and/or fiber optic output connectors) may be electrically connected (e.g., soldered) to outputs of the PCB of the spine coil housing 102. One or more corresponding output cables (e.g., output electrical cables and/or output fiber optic cables) may be in communication with and transmit the amplified and filtered MR signals from the one or more cable output connectors electrically connected to the outputs of the PCB of the spine coil housing 102. The one or more output electrical cables may be coaxial cables, and the electrical cable output connectors may be coaxial cable output connectors, for example. Alternatively, the outputs of the PCB are provided on a connector without further output cables in the spine coil housing 102. In one embodiment, the outputs of the PCB may be transmitted wirelessly.

The spine coil unit 100 includes one or more coil connectors 112 (e.g., two coil connectors). The coil connectors 112 may extend away from the third side 109 of the spine coil housing 102, in a direction generally perpendicular to the third side 109. "Generally" allows for other angles while still extending away from the third side 109 of the spine coil housing 102. The coil connectors 112 may be integrated with, attached to, physically connected to, adjacent to, or abut the third side 109 of the spine coil housing 102. The coil connectors 112 may extend from other sides, the top, and/or the bottom. The coil connectors 112 may be rigid, for example.

The coil connectors 112 each include a plurality of connectors 114 (e.g., input and output electrical connectors and/or input and output fiber optic connectors). The one or more output cables in communication with the PCB of the spine coil housing 102 may also be in communication with (e.g., soldered to) one or more of the output connectors 114 of the coil connectors 112. The plurality of electrical connectors 114 may include any number of connector types including, for example, pin connectors and cable connectors (e.g., coaxial cable connectors). The connections are releasable, such as using mated plugs. In one embodiment, the coil connectors 112 each include a locking mechanism such as, for example, a spring loaded plunger that matches a corresponding hole in an MRI system-side connector.

At least some of the output connectors 114 are electrically and/or optically connected to the RF receive coils of the spine coil housing 102 (e.g., via the PCB of the spine coil housing 102, and the electrical output cables). The output connectors 114 are configured to output the MR signals generated in the RF receive coils of the spine coil housing 102 and amplified and filtered in the low-noise amplifiers electrically connected to the PCB of the spine coil housing 102. The MR signals may be analog or digital signals (e.g., depending on whether the PCB of the spine coil housing 102 includes an analog to digital converter).

One or more of the input connectors 114 may be in communication with (e.g., electrically connected to or optically connected to) the PCB of the spine coil housing 102. For example, an input electrical connector 114 may be electrically connected to the PCB of the spine coil housing 102 with one or more corresponding electrical cables and/or wires soldered to the input electrical connector 114 and an input of the PCB of the spine coil housing 102. The one or more input connectors 114 may be configured to transmit data and/or power to control and power the electrical hardware components electrically connected to the PCB of the spine coil housing 102 (e.g., the one or more low-noise amplifiers).

The spine coil unit 100 also includes a lever 116 (shown in FIGS. 1-3) that is rotatably attached to the spine coil housing 102. The lever 116 includes a first side 118, a second side 120 and a bottom surface 122, and may be U-shaped, for example. Other shapes, such as linear, may be provided. The lever 116 may be made of any number of MRI-safe materials including, for example, Lexan 500 polycarbonate. In one embodiment, the spine coil unit 100 includes a plurality of levers 116. In another embodiment, the spine coil unit 100 does not include any levers 116.

The lever 116 may be rotatably attached at or adjacent to the third side 109 of the spine coil housing 102, at or adjacent to the first and second sides 118 and 120 of the lever 116. The lever 116 may be rotatably attached to the spine coil housing 102 using shafts attached to the lever 116 and corresponding holes in the spine coil housing 102 or ball bearings positioned in the spine coil housing 102. The lever 116 may be rotatable approximately 90° away from the spine coil housing 102, for example. "Approximately" allows for other rotations that are greater than 90° and less than 360° (e.g., 180°), or less than 90°. In one embodiment, the lever 116 is not rotatably attached to the spine coil housing 102 but is movably attached to the spine coil housing 102, such that the lever 116 moves telescopically away from and towards the top surface 104 of the spine coil housing 102.

The one or more coil connectors 112 may be physically attached to and electrically and/or optically connected to one or more corresponding MRI system-side connectors (not shown) in a support 124 (e.g., plug panel) of the MRI system. The connections are releasable, such as using mated plugs. The plug panel 124 may include a recess 126 shaped and sized for the lever 116. In an unlocked position, the lever 116 may extend away from the spine coil housing 102 in a direction generally parallel to the third side 109 of the spine coil housing 102. The lever 116 may be rotated away from the spine coil housing 102 into the recess 126 of the plug panel 124, such that the position of the spine coil housing 102 is fixed relative to the plug panel 124, and the physical attachment and the electrical connection between the one or more coil connectors 112 and the corresponding one or more MRI system-side connectors is maintained.

In one embodiment, the lever 116 is T-Shaped and is rotatably attached to the spine coil housing 102 at a single location on the spine coil housing 102. The T-Shaped lever 116 may be rotated into a corresponding T-shaped recess 126. In another embodiment, the lever 116 is circular-shaped and is not rotatably attached to the spine coil housing 102. The lever 116 may be positioned in the recess 126 and a corresponding recess in the top surface 104 of the spine coil housing 102.

The plug panel 124 may include a locking mechanism 128 located in the recess 126 of the plug panel 124. The locking mechanism 128 may be shaped and sized to match the shape and size of at least part of the lever 116, such that the lever 116 may be friction fit (e.g., locked) into the recess 126 of the plug panel 124. The locking mechanism 128 may include a spring (not shown) that maintains the friction fit between the locking mechanism 128 and the lever 116. The locking mechanism 128 may also include one or more tabs that may be depressed to release (e.g., unlock) the friction fit between the locking mechanism 128 and the lever 116. The locking mechanism 128 may be made of any number of MRI-safe materials including, for example, polycarbonate. Other locking mechanisms 128 including, for example, fasteners and Velcro strips may be used. In one embodiment, the plug panel 124 does not include the locking mechanism 128.

The one or more MRI system-side connectors include connectors (e.g., electrical connectors and/or optical connectors) that are in communication with and physically attached to corresponding connectors 114 of the one or more coil connectors 112. The MRI system includes a computer system that may include analog-to-digital converters in communication with the MRI system-side connectors to convert the filtered and amplified MR signals received at the MRI system-side connector from analog to digital signals (e.g., digitized MR signals).

The computer system of the MRI system may include a processor electrically connected to a memory and a display. The digitized MR signals may be stored in the memory and further processed by the processor for image reconstruction using, for example, a 2-dimensional Fourier transformation. The display may display the results of image reconstruction. The processor may include a plurality of general processors, digital signal processors, application specific integrated circuits, combinations thereof, or other now known or later developed processor. The memory may include one or more of a read only memory (ROM), dynamic random access memory (DRAM), an optical or magnetic storage device, or any other type of memory or data storage device. The display may be a cathode ray tube (CRT) display, a liquid crystal display (LCD) or a light emitting diode (LED) display, for example.

Figure 2:
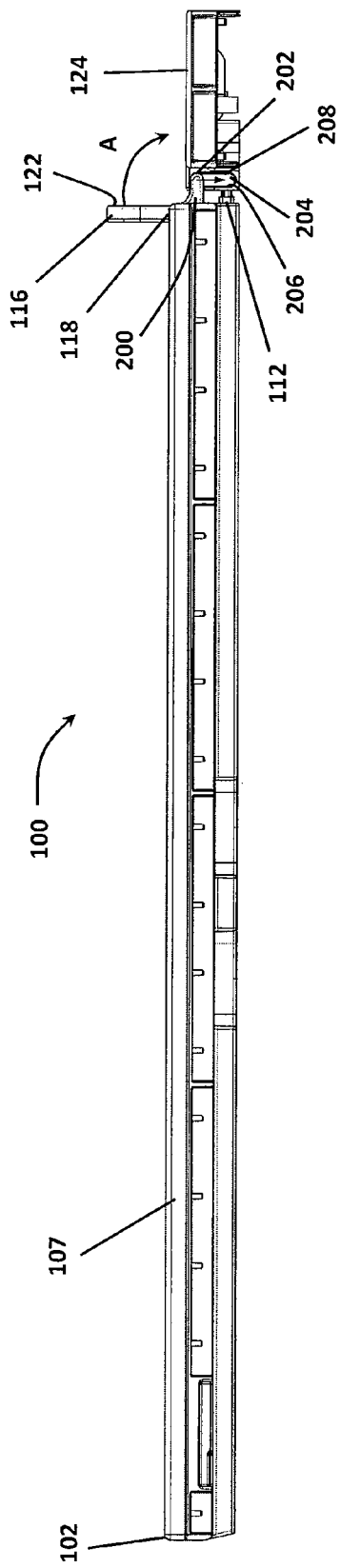
FIG. 2 illustrates a side view of one embodiment of a spine coil unit in an unlocked position.

FIG. 2 illustrates a side view of one embodiment of a spine coil unit 100 with a lever 116 in an unlocked position. The lever 116 rotatably attached to the spine coil housing 102 may include a first extension 200 extending from the bottom surface 122 of the lever 116 at the first side 118 of the lever 116, and a second extension (not shown) extending from the bottom surface 122 of the lever 116 at the second side 120 (shown in FIG. 1) of the lever 116. The first extension 200 and the second extension may extend away from the bottom surface 122 of the lever 116 in a direction generally perpendicular to the bottom surface 122 of the lever 116. "Generally" allows for other angles while still extending away from the bottom surface 122 of the lever 116. The first extension 200 and the second extension of the lever 116 (e.g., lever extensions) each include an end 202 that may be rounded, for example.

The plug panel 124 may include slots 204 shaped and sized, such that at least part of the first extension 200 and at least part of the second extension of the lever 116 fit in corresponding slots 204 of the plug panel 124. The slots 204 of the plug panel 124 are formed by a first wall 206 and a second wall 208 of the plug panel 124. The spine coil unit 100 may be disposed on the top surface of the patient table of the MRI system and slid along the top surface of the patient table until the ends 202 of the lever extensions 200 are adjacent to or abut the second wall 208 of the plug panel 124. The lever extensions 200 move into the corresponding slots 204 of the plug panel 124 when the lever 116 is rotated (e.g., arrow A) away from the spine coil housing 102, such that part of the lever extensions 200 abuts the first wall 206 of the plug panel 124. The lever extensions 200 and the slots 204 are sized and shaped, such that the motion of the lever extensions 200 against the first wall 206 of the plug panel 124 moves the one or more coil connectors 112 of the spine coil unit 100 into physical attachment and electrical and/or optical connection with the one or more MRI system-side connectors and/or fixes the position of the spine coil housing 102 relative to the position of the one or more MRI system-side connectors (i.e., locks the spine coil housing 102 to the plug panel 124). In one embodiment, the spine coil housing 102 includes one or more extensions that extend away from the third side 109 of the spine coil housing 102. The one or more extensions may be shaped and sized to fit into corresponding holes in the plug panel 124 to act as guides, for example.

Figure 3:
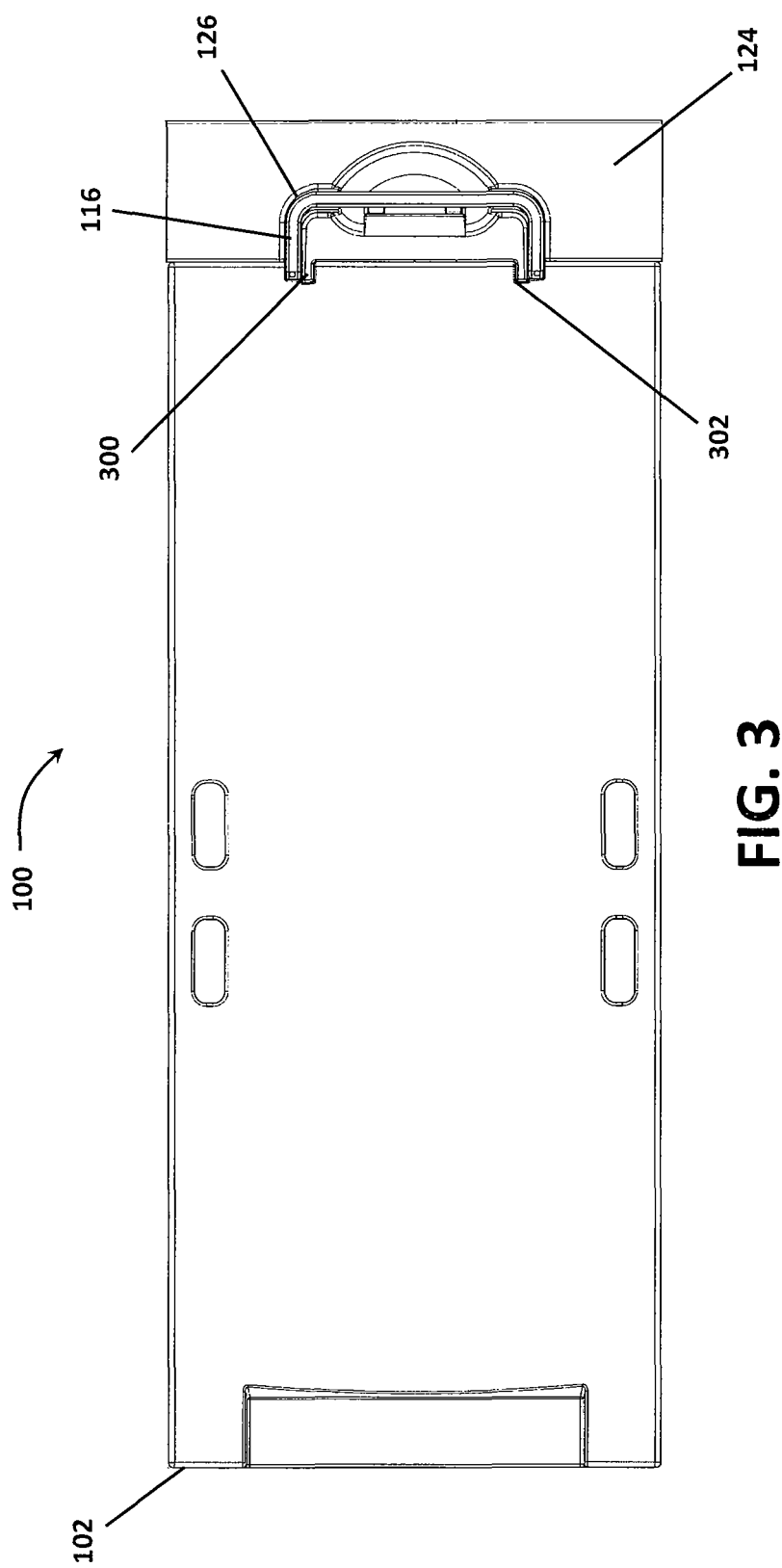
FIG. 3 illustrates a top view of one embodiment of a spine coil unit in a locked position.

FIG. 3 illustrates a top view of one embodiment of a spine coil 100 unit with a lever 116 in a locked position. In FIG. 3, the lever 116 has been rotated away from the spine coil housing 102 and into the recess 126 of the plug panel 124 to lock the spine coil unit 100 to the plug panel 124. The plug panel 124 includes one or more tabs 300 that are shaped and sized to be positioned into corresponding notches or recesses 302 in the spine coil housing 102 when the spine coil unit 100 is locked to the plug panel 124. In the locked position, part of the spine coil housing 102 may abut or be adjacent to part of the plug panel 124.

Rotating the lever 116 to move the spine coil unit 100 into electrical and/or optical connection with the MRI system may take less time than plugging individual coil connectors into corresponding MRI system-side connectors (as described in the prior art) to electrically and/or optically connect the spine coil unit 100 to the MRI system. External cables used to connect RF coils of a coil unit to coil connectors (e.g., as in the prior art) may pose a safety risk (e.g., burns) to patients and may be damaged during transfer to and from a storage location. These potential risks may be avoided with the use of the lever 116 in combination with the one or more coil connectors 112 extending from the third side 109 of the spine coil housing 102. The spine coil unit 100 of the present embodiments may also be less expensive than a coil unit that includes external cables. The features described for the spine coil unit 100 may be applied to coil units for different applications (e.g., breast coil units).

Figure 4:
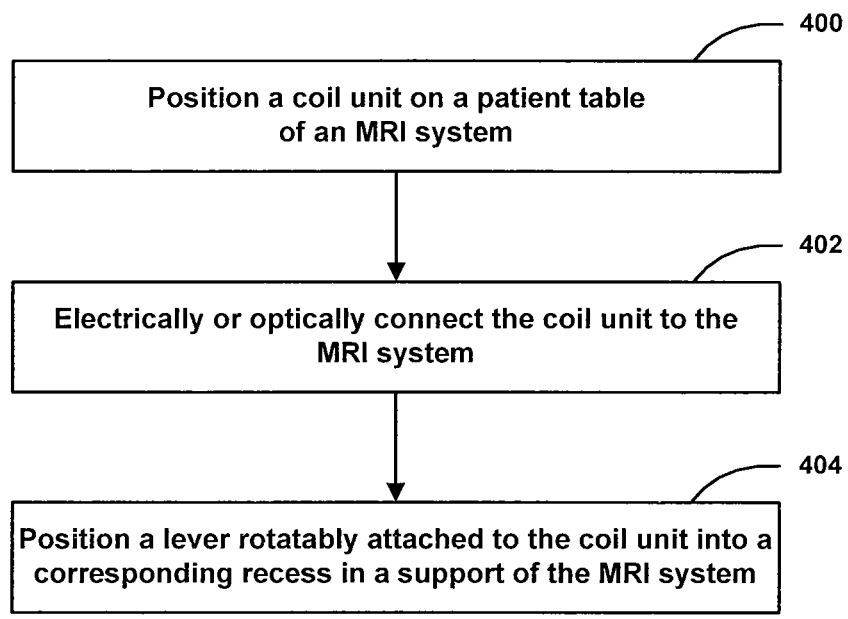
FIG. 4 illustrates a flow chart of one embodiment of a method of using a coil unit.

FIG. 4 illustrates a flow chart of one embodiment of a method of using one embodiment of the spine coil unit 100 shown in FIGS. 1-3 or a different coil unit. The method is implemented in the order shown, but other orders may be used. Additional, different, or fewer acts may be provided.

At block 400, a coil unit is positioned on a patient table of a magnetic resonance imaging (MM) system. The coil unit may include a coil housing that includes a top surface, a bottom surface and a front side. The bottom surface of the coil housing may be shaped and sized to match at least part of a u-shaped channel formed by a top surface of the patient table. The top surface of the coil housing may be concave, such that the spine of a patient lying on the patient table may align with the central longitudinal axis of the coil unit (e.g., a spine coil unit). The coil housing may be made of any number of MRI-safe materials including, for example, Lexan 500 polycarbonate.

The coil housing includes a plurality of RF coils (e.g., 32 RF coils). The plurality of RF coils may be surface coils and are supported by or attached to an internal surface of the coil housing. The RF coils of the coil housing may be RF receive coils and/or RF transmit coils. The RF coils may be made of any number of materials including, for example, copper.

The coil unit includes a rigid coil connector extending away from the front or other side of the coil housing, in a direction perpendicular to the side of the coil housing. The coil connector includes a plurality of electrical connectors (e.g., input and output connectors). At least some of the electrical connectors of the plurality are electrically and/or optically connected to the plurality of RF coils of the coil housing via one or more electrical cables and/or a PCB supported by an internal surface of the coil housing. One or more low-noise amplifiers may be electrically connected (e.g., soldered) to the PCB of the coil housing to amplify and filter the magnetic resonance signals (MR) received at the plurality of RF coils of the coil housing. The coil housing may include more rigid coil connectors extending away from the front side of the coil housing and including electrical connectors electrically connected to at least some of the RF coils of the coil housing.

The coil unit also includes a lever (e.g., toggle lever) rotatably attached to the coil housing, at or adjacent to the front or other side of the coil housing. The lever may be u-shaped, for example, and may be rotatably attached to the coil housing at two sides of the u-shaped lever. The lever may include extensions that extend away from a bottom surface of the lever in a direction perpendicular to the bottom surface of the lever. The lever may be made of any number of MRI-safe materials including, for example, Lexan 500 polycarbonate. In one embodiment, the lever may not include extensions. In other embodiments, the lever may be t-shaped or circular.

The coil unit may be moved along the u-shaped channel formed by the top surface of the patient table, such that the extensions of the lever are adjacent to or abut rear walls of corresponding guide slots (e.g., spaced the same distance as the extensions of the lever) in a support of the MM system (e.g., a plug panel). The guide slots of the plug panel may be shaped and sized, such that the extensions of the lever may fit in the guide slots.

At block 402, the coil unit is electrically or optically connected to the MM system. Since the bottom surface of the coil housing may be shaped and sized to match at least part of the u-shaped channel of the patient table, the coil connector of the coil unit may be aligned with a corresponding MRI system-side connector when the coil housing is positioned in the channel of the patient table. The coil unit may be moved along the u-shaped channel of the patient table, such that the coil connector of the coil unit is physically attached to and electrically connected to the corresponding MRI system-side connector.

At block 404, the lever rotatably attached to the coil unit is positioned into a corresponding recess in the support of the MRI system. The lever may be rotated 90° away from the top surface of the coil housing from an unlocked position (i.e., with the lever extending away from the top surface of the coil housing, in a direction parallel to the front of the coil housing) to a locked position. The extensions of the lever may rotate into the guide slots of the plug panel when the lever is rotated into the corresponding recess in the plug panel. During rotation of the lever, the extensions of the lever may abut front walls of the guide slots, thus moving the coil connector of the coil unit into physical attachment and electrical and/or optical connection with the corresponding MRI system-side connector and/or fixing the position of the coil connector relative to the position of the corresponding MRI system-side connector.

The recess in the support of the MRI system may include a locking mechanism that forms a friction fit with part of the lever when the lever is rotated into the recess. Other locking mechanisms including fasteners and Velcro, for example, may be used.

Various embodiments described herein can be used alone or in combination with one another. The foregoing detailed description has described only a few of the many possible implementations of the present invention. For this reason, this detailed description is intended by way of illustration, and not by way of limitation.

The invention claimed is:

1. A radiofrequency (RF) coil unit comprising:
a coil housing comprising a first side;
an RF coil disposed in the coil housing;
a lever movably attached to the coil housing; and
a rigid coil connector extending away from the first side of the coil housing, the rigid coil connector being in communication with the RF coil of the coil housing,
wherein the lever is operable to be moved into a corresponding recess in a support of a magnetic resonance imaging (MRI) system, the movement of the lever into the corresponding recess causing movement of the coil housing along a patient table supporting the coil housing, the rigid coil connector being physically attached to and in communication with a connector of a data acquisition system of the MRI system and a position of the coil housing being fixed relative to a position of the connector of the data acquisition system of the MRI system after the movement of the lever into the corresponding recess.

2. The RF coil unit of claim 1, wherein the RF coil of the coil housing is a surface coil.

3. The RF coil unit of claim 1, wherein the coil housing comprises a plurality of RF coils disposed in the coil housing, and
wherein the plurality of RF coils of the coil housing is arranged in a plurality of RF coil arrays.

4. The RF coil unit of claim 1, wherein the lever is rotatably attached to the coil housing, and
wherein the lever is operable to rotate ninety degrees.

5. The RF coil unit of claim 1, wherein the rigid coil connector is in optical communication with the connector of the data acquisition system of the MRI system.

6. The RF coil unit of claim 1, wherein the rigid coil connector extends away from the first side in a direction perpendicular to the first side.

7. A spine coil unit comprising:
a spine coil housing;
a radiofrequency (RF) coil disposed in the spine coil housing, the RF coil being configured to receive magnetic resonance signals emitted by a patient supported by the spine coil housing;
a lever rotatably attached to the spine coil housing; and
a coil connector physically connected to the spine coil housing and in communication with the RF coil of the spine coil housing,
wherein the lever is operable to be rotated into a corresponding recess in a support of a magnetic resonance imaging (MRI) system, such that the position of the spine coil housing is fixed relative to the position of a connector of the MRI system the MRI system, the rotation of the lever into the corresponding recess causing movement of the spine coil housing along a patient table supporting the spine coil housing, the coil connector being physically attached to and in communication with the connector of the MRI system after the rotation of the lever into the corresponding recess.

8. The spine coil unit of claim 7, wherein the lever is operable to rotate ninety degrees.

9. The spine coil unit of claim 7, wherein the coil connector is operable to be electrically or optically connected to the connector of the MRI system, and
wherein the lever is operable to move the coil connector into physical attachment and electrical or optical connection with the connector of the MRI system.

10. The spine coil unit of claim 9, wherein the spine coil housing comprises a side, and
wherein the coil connector extends away from the side of the spine coil housing in a direction perpendicular to the side of the spine coil housing.

11. The spine coil unit of claim 7, further comprising 32 RF coils disposed in the spine coil housing.

12. The spine coil unit of claim 7, wherein the RF coil is a volume coil.

13. The spine coil unit of claim 7, wherein the support of the MRI system comprises a locking mechanism at least partly disposed in the recess, and
wherein the locking mechanism is operable to fix the rotational position of the lever relative to a top surface of the spine coil housing.

14. A method of using a coil unit, the method comprising:
positioning the coil unit on a patient table of a magnetic resonance imaging (MRI) system, the coil unit comprising a radiofrequency (RF) coil;
physically attaching and electrically or optically connecting a coil connector electrically or optically connected to the RF coil of the coil unit to a connector of the MRI system; and
positioning a lever rotatably attached to the coil unit into a corresponding recess in a support of the MRI system such that the physically attaching and the electrically or optically connecting is maintained in place by the lever, the positioning of the lever into the corresponding recess moving the coil unit along the patient table, the coil connector being physically attached and electrically or optically connected to the connector of the MRI system after the positioning of the lever into the corresponding recess.

15. The method of claim 14, wherein positioning the coil unit comprises positioning the coil unit in a channel of the patient table of the MRI system.

16. The method of claim 15, wherein physically attaching and electrically or optically connecting the coil unit to the MRI system comprises sliding the coil unit along the channel of the patient table, such that the coil connector electrically or optically connected to the RF coil of the coil unit is physically attached to and electrically or optically connected to the connector of the MRI system.

17. The method of claim 16, wherein positioning the lever comprises rotating the lever into the corresponding recess in the support of the MRI system, such that a position of the coil unit is fixed relative to the position of the connector of the MRI system.

18. The method of claim 16, wherein positioning the lever into the corresponding recess in the support of the MRI system moves the coil unit along the channel of the patient table, such that the coil connecter physically attaches to and electrically connects to the connector of the MRI system.

* * * * *